United States Patent
Johnson

(10) Patent No.: US 9,526,566 B1
(45) Date of Patent: Dec. 27, 2016

(54) ELECTROSURGICAL DEVICES WITH PHASE CHANGE MATERIALS

(71) Applicant: Ethicon Endo-Surgery, LLC, Guaynabo, PR (US)

(72) Inventor: Eric Johnson, Maineville, OH (US)

(73) Assignee: Ethicon Endo-Surgery, LLC, Guaynabo, PR (US)

(*) Notice: Subject to any disclaimer, the term of this patent is extended or adjusted under 35 U.S.C. 154(b) by 197 days.

(21) Appl. No.: 14/314,824

(22) Filed: Jun. 25, 2014

(51) Int. Cl.
  *A61B 18/14* (2006.01)
  *A61B 18/00* (2006.01)

(52) U.S. Cl.
  CPC .. *A61B 18/1445* (2013.01); *A61B 2018/00053* (2013.01); *A61B 2018/1455* (2013.01)

(58) Field of Classification Search
  CPC ............ A61B 18/1442; A61B 18/1445; A61B 18/1447; A61B 2018/1452; A61B 2018/1455; A61B 2018/1457
  See application file for complete search history.

(56) References Cited

U.S. PATENT DOCUMENTS

| | | | |
|---|---|---|---|
| 2006/0004356 A1* | 1/2006 | Bilski | A61B 18/1442 606/51 |
| 2008/0294222 A1* | 11/2008 | Schechter | A61B 18/1445 607/50 |
| 2014/0094801 A1 | 4/2014 | Boudreaux et al. | |

OTHER PUBLICATIONS

[No Author Listed] TPCM™ FSF-52. Laird Technologies. Product Data Sheet. 2010, 1 page.
[No Author Listed] TPCM™ HP105 Series, Phase Change Material. Laird Technologies. Product Data Sheet. 2010, 1 page.

* cited by examiner

*Primary Examiner* — Jaymi Della
(74) *Attorney, Agent, or Firm* — Nutter McClennen & Fish LLP

(57) ABSTRACT

Electrosurgical devices are disclosed herein in which one or more electrodes are separated from adjacent portions of the device by a phase change material. The phase change material can be a solid at room temperature that melts at operating temperatures, forming intimate contact at the interface between the electrode and the adjacent portion of the device to produce low thermal resistance. The phase change material can have a high dielectric strength which electrically isolates the electrode from adjacent portions of the device while simultaneously providing low thermal resistance. Above a predetermined threshold temperature, the phase change material can change into a molten state and wet the joint surfaces to create a thin, low thermal resistance interface. The phase change material can be thixotropic and can be relatively viscous when in liquid form such that the material does not flow or otherwise migrate from the interface during operation.

19 Claims, 3 Drawing Sheets

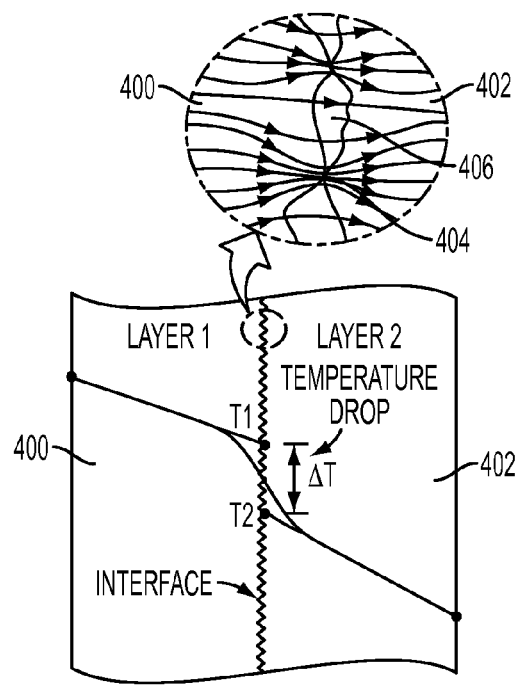
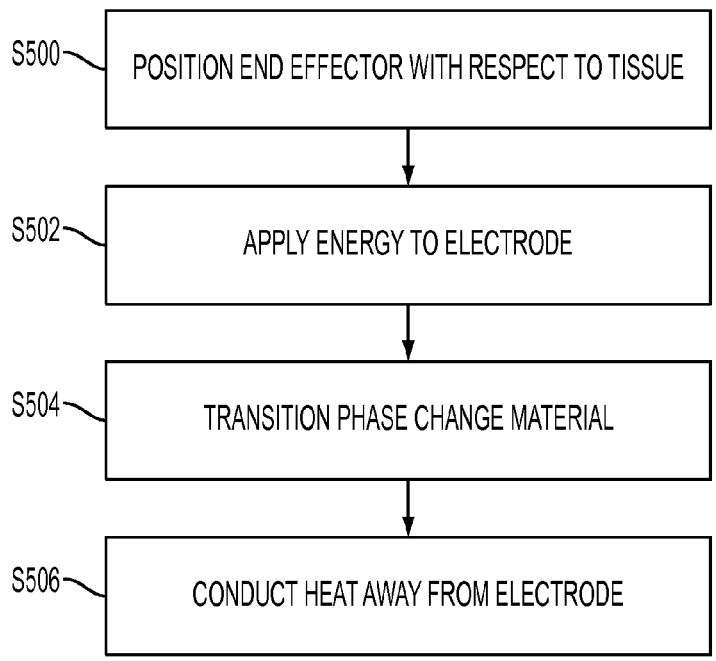
FIG. 4
FIG. 5

ELECTROSURGICAL DEVICES WITH PHASE CHANGE MATERIALS

FIELD

Electrosurgical devices with phase change materials and related methods are disclosed herein.

BACKGROUND

Electrosurgical devices are used in many surgical operations. Electrosurgical devices can apply electrical energy to tissue in order to treat the tissue. An exemplary electrosurgical device can include a distally-mounted end effector having one or more electrodes. The end effector can be positioned against tissue such that electrical current is introduced into the tissue. Electrosurgical devices can be configured for bipolar and/or monopolar operation. During bipolar operation, current is introduced into and returned from the tissue by active and return electrodes, respectively, of the end effector. During monopolar operation, current is introduced into the tissue by an active (or source) electrode of the end effector and returned through a return electrode (e.g., a grounding pad) separately located on a patient's body. Heat generated by the current flow through the tissue can form hemostatic seals within the tissue and/or between tissues and thus can be particularly useful for sealing blood vessels, for example. The end effector of an electrosurgical device can also include a cutting knife that is movable relative to the tissue and the electrodes to transect the tissue.

Electrical energy applied by an electrosurgical device can be transmitted to the device by a generator. The electrical energy can be in the form of radio frequency (RF) energy. RF energy is a form of electrical energy that can be in the frequency range of about 100 kHz to about 1 MHz. During operation, an electrosurgical device can transmit low frequency RF energy through tissue, which can cause ionic agitation, friction, and/or resistive heating, thereby increasing the temperature of the tissue. Because a sharp boundary can be created between the affected tissue and the surrounding tissue, surgeons can operate with a high level of precision and control without sacrificing un-targeted adjacent tissue. The low operating temperatures of RF energy can be useful for removing, shrinking, or sculpting soft tissue while simultaneously sealing blood vessels. RF energy can work particularly well on connective tissue, which is primarily comprised of collagen and shrinks when contacted by heat.

Thermal management can be an important factor in the design and operation of electrosurgical devices. If heat is dissipated from the electrode into adjacent portions of the device too quickly, more time can be required to seal the tissue and the seal quality can be adversely affected. For example, in the case of a sealed vessel, the burst pressure of the seal can be too low if the electrode is not hot enough when the seal is formed. If heat is dissipated from the electrode into adjacent portions of the device too slowly, the electrode temperature can increase beyond an ideal range, which can undesirably cause tissue to burn and stick to the electrode. In practice, it can be difficult to regulate the transfer of heat from the electrode with high precision.

There is a continuing need for improved electrosurgical devices and related methods.

SUMMARY

Electrosurgical devices are disclosed herein in which one or more electrodes are separated from adjacent portions of the device by a phase change material. The phase change material can be a solid at room temperature that melts at operating temperatures, forming intimate contact at the interface between the electrode and the adjacent portion of the device to produce low thermal resistance. The phase change material can have a high dielectric strength which electrically isolates the electrode from adjacent portions of the device while simultaneously providing low thermal resistance. This combination of thermal and electrical properties can alleviate the need for additional material layers providing electrical isolation of the electrode. Above a predetermined threshold temperature, the phase change material can change into a molten state and wet the joint surfaces to create a thin, low thermal resistance interface. The phase change material can be thixotropic and can be relatively viscous when in liquid form such that the material does not flow or otherwise migrate from the interface during operation.

In some embodiments, an electrosurgical device includes a handle portion, an elongate shaft extending distally from the handle portion, and an end effector coupled to a distal end of the elongate shaft, the end effector comprising a first jaw member, a first electrode, and a first phase change material (PCM) member disposed between the first jaw member and at least a portion of the first electrode.

The first PCM member can include a first surface to which at least a portion of the first electrode is attached and a second, opposite surface to which at least a portion of the first jaw is attached. The end effector can include a second jaw member, a second electrode, and a second PCM member disposed between the second jaw member and at least a portion of the second electrode. The first and second jaw members can define a longitudinal channel, the end effector comprising a cutting knife slidably receivable within the longitudinal channel, wherein the cutting knife is deployable along the longitudinal channel. The first PCM member can be or can include a planar sheet. The first PCM member can be formed from a ceramic filled wax. The first PCM member can have a phase change temperature of about 50 degrees C. to about 60 degrees C. The first PCM member can have any of a variety of thicknesses. For example, the first PCM member can have a thickness of about 0.003 inches to about 0.100 inches. By way of further example, the first PCM member can have a thickness of about 0.005 inches to about 0.020 inches. As another example, the first PCM member can have a thickness of about 0.010 inches to about 0.015 inches. The first PCM member can be or can include a thixotropic material. The first PCM member can incorporate an adhesive layer to aid in assembly and manufacture of the electrosurgical device. The first PCM member can be configured to wet the first electrode and the first jaw member when in use without flowing from an interface between the first electrode and the first jaw member. The first PCM member and the first electrode can be laminated to the first jaw. The first PCM member can be a solid at room temperature and a liquid at operating temperatures. The end effector can be operable to deliver at least one of monopolar electrosurgical energy, bipolar electrosurgical energy, ultrasonic energy, thermal energy, and combinations thereof. The first PCM member can be thermally conductive with high dielectric strength, providing electrical isolation between the first jaw member and at least a portion of the first electrode.

In some embodiments, an end effector includes a first jaw assembly comprising a first body portion and a first electrode, at least a portion of the first electrode being separated from the first body portion by a first layer of phase change material, and a second jaw assembly comprising a second body portion and a second electrode, wherein the first jaw assembly and the second jaw assembly are operatively coupled to one another such that tissue can be grasped between the first and second electrodes and such that energy can be delivered to the tissue through at least one of the first and second electrodes.

At least a portion of the second electrode can be separated from the second body portion by a second layer of phase change material. The first layer of phase change material can be formed from a ceramic filled wax. The first layer of phase change material can be configured to wet the first electrode and the first body portion when in use without flowing from an interface between the first electrode and the first body portion.

In some embodiments, a method of delivering energy to tissue includes positioning an electrosurgical device having a jaw member with an electrode that is spaced from the jaw member by a layer of phase change material such that the electrode is in contact with the tissue, and applying energy to the tissue and to the electrode, thereby heating the electrode and transitioning the layer of phase change material to a liquid through which heat is conducted away from the electrode and into the jaw member.

The present invention further provides devices and methods as claimed.

BRIEF DESCRIPTION OF THE DRAWINGS

The invention will be more fully understood from the following detailed description taken in conjunction with the accompanying drawings, in which:

FIG. 4 is a schematic illustration of an electrode-jaw interface without a phase change material; and FIG. 5 is a flow chart of an exemplary method of using an electrosurgical device.

DETAILED DESCRIPTION

Electrosurgical devices are disclosed herein in which one or more electrodes are separated from adjacent portions of the device by a phase change material. The phase change material can be a solid at room temperature that melts at operating temperatures, forming intimate contact at the interface between the electrode and the adjacent portion of the device to produce low thermal resistance. The phase change material can have a high dielectric strength which electrically isolates the electrode from adjacent portions of the device while simultaneously providing low thermal resistance. This combination of thermal and electrical properties can alleviate the need for additional material layers providing electrical isolation of the electrode. Above a predetermined threshold temperature, the phase change material can change into a molten state and wet the joint surfaces to create a thin, low thermal resistance interface. The phase change material can be thixotropic and can be relatively viscous when in liquid form such that the material does not flow or otherwise migrate from the interface during operation.

Certain exemplary embodiments will now be described to provide an overall understanding of the principles of the structure, function, manufacture, and use of the devices and methods disclosed herein. One or more examples of these embodiments are illustrated in the accompanying drawings. Those of skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Figure 1:
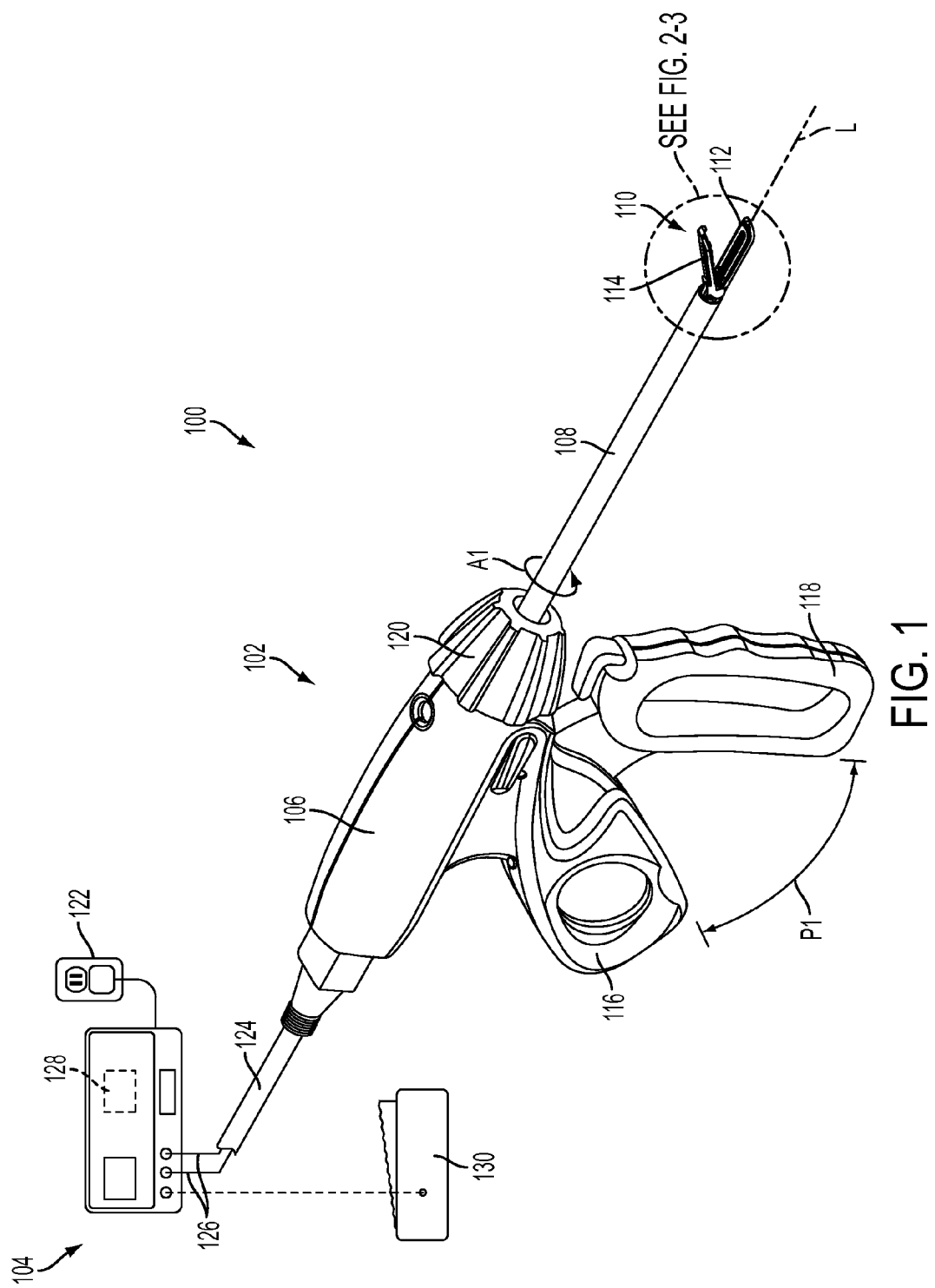
FIG. 1 is a schematic perspective view of an exemplary surgical system.

FIG. 1 illustrates an exemplary embodiment of a surgical system 100. The system 100 can be configured to supply energy, such as electrical energy, ultrasonic energy, heat energy, or any combination thereof, either independently or simultaneously, to the tissue of a patient. The system 100 generally includes an electrosurgical device 102 and a generator 104.

The electrosurgical device 102 can include a proximal handle portion 106, an elongate body or shaft portion 108, and an end effector 110 coupled to a distal end of the elongate shaft. In the illustrated embodiment, the end effector 110 includes first and second jaws 112, 114 configured to grasp tissue. It will be appreciated, however, that in some embodiments the end effector 110 can include only a single jaw, for example in the case of a monopolar electrosurgical device. As discussed further below, the jaws 112, 114 can include one or more electrodes for delivering energy to tissue clamped between the jaws, and a cutting knife for transecting said tissue.

The handle portion 106 can include a fixed handle 116 and a lever arm or trigger 118 which can be pulled along a path P1. The lever arm 118 can be coupled to an axially moveable actuation shaft, cable, or other actuation mechanism disposed within the elongate shaft 108 and configured to open and/or close the jaws 112, 114 of the end effector 110. For example, an actuation shaft can be urged distally as the lever arm 118 is pulled proximally along the path P1 to close the jaws 112, 114 and/or to advance the cutting knife of the end effector 110. The handle portion 106 can be any type of pistol-grip or other handle known in the art that is configured to carry actuator levers, triggers, sliders, and so forth for actuating the first and second jaws 112, 114, advancing the knife, and initiating energy delivery. In some embodiments, the handle portion 106 can be or can include a pencil-style handle.

The elongate shaft 108 can have a cylindrical or rectangular cross-section and can include at least one inner lumen through which the actuation shaft and electrical leads for delivering energy to the end effector 110 can extend. In some embodiments, the elongate shaft 108 can be a thin-walled tubular sleeve that extends distally from the handle portion 106. In some embodiments, the elongate shaft 108, along with the end effector 110 coupled thereto, can be rotatable a full 360 degrees, as shown by the arrow A1, relative to the handle portion 106. For example, a rotation knob or nozzle 120 can be rotatable about the longitudinal axis L of the shaft 108 and can be coupled to the shaft such that rotation of the knob causes corresponding rotation of the shaft. The jaws 112, 114 of the end effector 110 can remain openable and/or closeable while rotated.

The generator 104 can be a separate component as shown or can be incorporated or integrated into the electrosurgical device 102. The generator 104 can be battery powered or can be coupled to a wall outlet 122 or other power source. The generator 104 can be connected to the device via a suitable transmission medium such as a cable 124 having one or more electrical conductors 126 disposed therein (e.g., a first conductor electrically coupled to an active electrode of the device and a second conductor electrically coupled to a return electrode of the device). The generator 104 can be configured to apply a voltage differential across the first and second conductors to cause current to flow through the device 102 and tissue disposed between the jaws 112, 114. The generator 104 can be or can include an RF source, an ultrasonic source, a direct current source, and/or any other suitable type of electrical energy source.

The generator 104 can include a control unit 128 that regulates the electrical energy delivered to the device 102. Energy delivery can be initiated by a switching mechanism, such as an activation button operably engaged with the lever arm 118 and in electrical communication with the generator 104 via the cable 124. Other switching mechanisms can be used instead or in addition, such as a thumb switch mounted on the handle portion 106 or a foot switch 130.

The generator 104 can be implemented as an electrosurgery unit (ESU) capable of supplying power sufficient to perform bipolar electrosurgery using radio frequency (RF) energy. For example, the ESU can be a bipolar ERBE ICC 150 sold by ERBE USA, Inc. of Marietta, Ga. In some embodiments, such as for bipolar electrosurgery applications, the device 102 can include an active electrode and a return electrode, wherein the active electrode and the return electrode can be positioned against, adjacent to and/or in electrical communication with, the tissue to be treated such that current can flow from the active electrode to the return electrode through the tissue. Thus, the system 100 can include a supply path and a return path, wherein the captured tissue being treated completes, or closes, the circuit. The generator 104 can also be a monopolar RF ESU and the electrosurgical device 102 can include a monopolar end effector 110 in which one or more active electrodes are disposed. In such embodiments, the system 100 can include a return pad in intimate contact with the patient at a location remote from the operative site and/or another suitable return path. The return pad can be connected via a cable to the generator 104.

Figure 2:
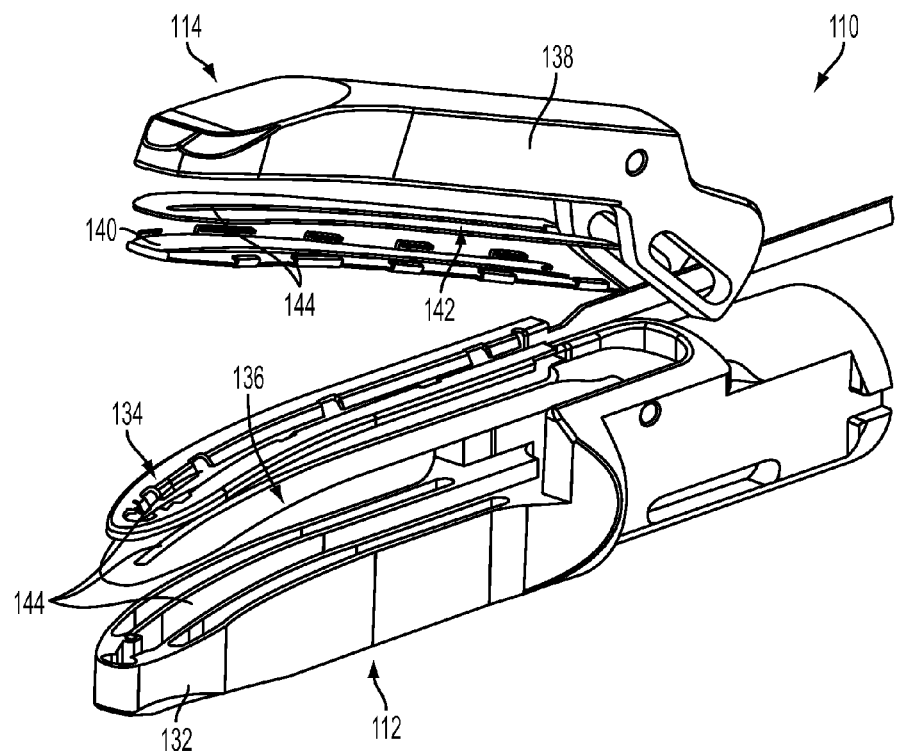
FIG. 2 is a perspective exploded view of an end effector of the system of FIG. 1.
Figure 3:
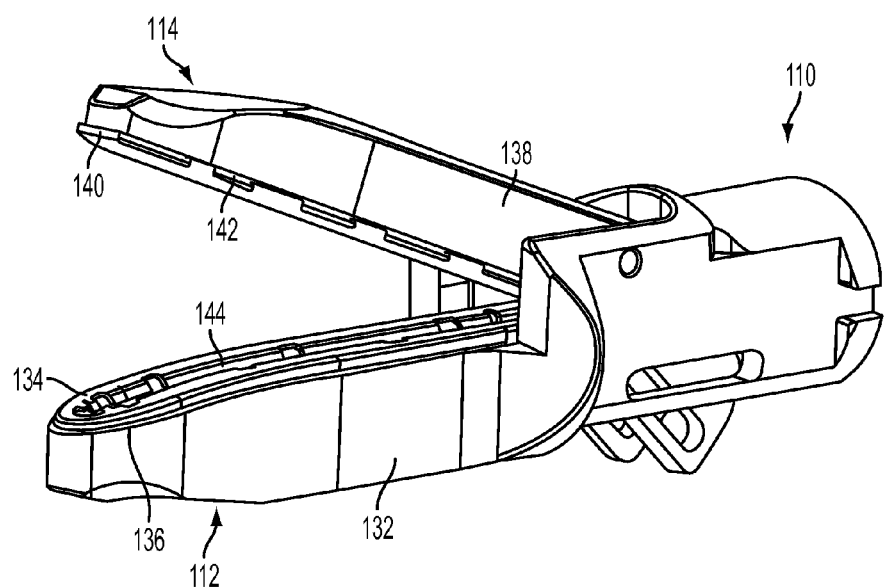
FIG. 3 is a perspective assembled view of the end effector of FIG. 2.

The end effector 110 can be configured to capture and transect tissue and to contemporaneously weld the captured tissue with controlled application of energy (e.g., RF energy). As shown in FIGS. 2-3, the first jaw 112 of the end effector 110 can include a first body portion 132, an active electrode 134, and a first phase change material (PCM) member 136, and the second jaw 114 of the end effector can include a second body portion 138, a return electrode 140, and a second PCM member 142.

The active and return electrodes 134, 140 can define opposed energy delivery surfaces configured to capture or engage tissue and to apply compression to the tissue when the jaws 112, 114 are closed. In the illustrated embodiment, the first jaw 112 is fixed relative to the elongate shaft 108 and the second jaw 114 is pivotally coupled to the first jaw. In other embodiments, the second jaw 114 can be fixed and the first jaw 112 can be pivotally coupled thereto, or both jaws can be pivotally coupled to one another or to the elongate shaft 108. It will also be appreciated that the location of the active and return electrodes 134, 140 can be reversed, such that the active electrode is instead coupled to the second jaw 114 and such that the return electrode is instead coupled to the first jaw 112. The jaws 112, 114 and the energy delivery surfaces can be straight or can be curved in one or more planes. The jaws, PCM members, and electrodes can include aligned longitudinal slots or channels 144 through which a cutting knife (not shown) can be advanced to cut tissue clamped between the jaws.

The active and return electrodes can at least in part be formed from or coated with a conductive-resistive matrix, such as a variable-resistive positive-temperature-coefficient (PTC) material. The PTC material can limit the energy delivered by the energy delivery surfaces of the electrodes as the temperature of said surfaces increases during treatment. The energy delivery surfaces can be configured to provide therapeutic RF energy, sub-therapeutic RF energy, ultrasonic energy, or any combination thereof.

At least a portion of the active electrode 134 can be separated from the first body portion 132 by the first PCM member 136. The active electrode can be coupled to the first PCM member which can be coupled to the first body portion. In particular, the active electrode can be attached to an upper surface of the first PCM member and the first body portion can be attached to a lower surface of the first PCM member. Similarly, at least a portion of the return electrode 140 can be separated from the second body portion 138 by the second PCM member 142. The return electrode can be coupled to the second PCM member which can be coupled to the second body portion. In particular, the return electrode can be attached to a lower surface of the second PCM member and the second body portion can be attached to an upper surface of the second PCM member.

The end effector 110 can thus employ a laminated construction in which each PCM member 136, 142 constitutes a layer of thermal interface material interposed between the respective electrodes 134, 140 and the body portions 132, 138 of the jaws 112, 114. The various components of the end effector 110 can be coupled to one another in any of a variety of ways, including using adhesives, interference or snap-fit connections, welded connections, screws, etc. In operation, the body portions of the jaws act as heat sinks, extracting heat from the electrodes. As described further below, the PCM members can reduce the thermal contact resistance between the electrodes and the jaws, improving heat transfer. While the electrodes and jaws are directly coupled to the PCM members in the illustrated embodiment, it will be appreciated that intermediate members can be included in some instances. For example, electrically-insulating layers can be disposed between one or both of the PCM members and the jaws and/or between one or both of the PCM members and the electrodes. In some embodiments, the PCM members can have a high dielectric strength which electrically isolates the electrodes from adjacent portions of the device while simultaneously providing low thermal resistance. This combination of thermal and electrical properties can alleviate the need for additional material layers providing electrical isolation of the electrodes. In some embodiments, the end effector can include only a single PCM member (e.g., only on the first jaw or only on the second jaw).

The PCM members can be at least in part formed of, coated with, or impregnated with a phase change material and can be configured to minimize the thermal contact resistance between the electrodes and the jaws. In the absence of the PCM members, as shown in FIG. 4, surface irregularities would create an uneven contact interface between the electrode 400 and the jaw 402, characterized by point contacts 404 where heat is transferred easily and voids 406 where heat is not easily transferred. The uneven interface would result in increased thermal contact resistance which would preclude efficient heat transfer between the electrode 400 and the jaw 402 and make it difficult to regulate transfer of heat from the electrode with high precision. While greases with filler media can be applied between the electrode and the jaw to increase the thermal conductivity across the interface, grease can be messy and preventing cross-contamination can be challenging. In particular, greases can be difficult to apply and can undesirably flow out of the interface when the device is being used.

The PCM members 136, 142, on the other hand, can better control contact resistance and achieve more uniform heat conduction to better manage heat transfer from the electrodes 134, 140 into the main body portions 132, 138 of the jaws 112, 114. Phase change materials used in constructing the PCM members are also available in a sheet product that is much easier to apply than greases.

The phase change material used in the PCM members can be a solid at room temperature that melts at operating temperatures, forming intimate contact on the mating surfaces to produce low thermal resistance. The phase change material can be a free standing film that contains no substrate. Above a predetermined threshold temperature (e.g., about 52 degrees C.), the phase change material can change into a molten state and, under low closure force, wet the electrode and jaw surfaces to create a thin, low thermal resistance interface. The phase change material can be thixotropic and can be relatively viscous when in liquid form such that the material does not flow or otherwise migrate from the interface during operation. The phase change material can have superior thermal performance comparable to the highest performing grease. In addition, since the phase change material can be a free standing film, it can be easy to handle and apply. The phase change material can be produced as individual die cut parts, kiss cut parts on rolls or sheets, or in uncut rolls. The phase change material can also be produced with or without adhesive surfaces for attaching the PCM members to the electrodes and/or jaws.

Any of a variety of phase change materials can be used, including, by way of non-limiting example, ceramic filled waxes such as Tpcm™ FSF-52 and Tpcm™ HP105 series materials available from Laird Technologies.

The PCM members can thus provide reduced thermal contact resistance at the interface between the electrodes and the jaws forming a thixotropic liquid during use which fully wets the substrate materials at operating temperatures without flowing or migrating from the substrate interface. As used herein, the "operating temperature" of an electrosurgical device is the temperature or range of temperatures experienced by the electrodes when the device is used for its intended purpose (e.g., to cut, coagulate, or seal tissue in connection with a surgical procedure, etc.). In some embodiments, operating temperatures of the device are greater than room temperature and greater than normal body temperature.

The dimensions and composition of the PCM members can be selected to provide the desired thermal conductivity. In some embodiments, the PCM members are planar sheets which can be curved or bent to match the contour of the jaws and/or electrodes. The PCM members can have any of a variety of thicknesses. For example, the PCM members can have a thickness of about 0.003 inches to about 0.100 inches. By way of further example, the PCM members can have a thickness of about 0.005 inches to 0.050 inches. As another example, the PCM members can have a thickness of about 0.007 inches to 0.030 inches. As yet another example, the PCM members can have a thickness of about 0.005 inches to about 0.020 inches. By way of further example, the PCM members can have a thickness of about 0.010 inches to about 0.015 inches. The thickness of the PCM members can also vary based on the jaw geometry, the type of tissue with which the device is to be used, and/or other factors. Larger jaws which have more surface area contact with the PCM members are able to extract more heat and therefore the thickness of the PCM members can be reduced.

The phase change temperature of the PCM members can be chosen to correspond with typical operating temperatures of the electrosurgical device. The PCM members can have a phase change or threshold temperature of about 50 degrees C. to about 60 degrees C. For example, the PCM members can have a phase change or threshold temperature of about 52 degrees C.

The thermal conductivity of the PCM members can be chosen based on jaw size, electrode surface area, and/or other parameters to achieve an optimal rate of heat transfer away from the electrode. For example, the PCM members can have a thermal conductivity of about 0.5 W/mK to about 1.5 W/mK. By way of further example, the PCM members can have a thermal conductivity of about 0.6 W/mK to about 1.2 W/mK. As another example, the PCM members can have a thermal conductivity of about 0.73 W/mK. As yet another example, the PCM members can have a thermal conductivity of about 0.9 W/mK. The thermal conductivity of the PCM members can be measured using the ASTM D5470 test method.

The PCM members can be electrically-insulating or electrically-conductive. For example, both of the PCM members can be electrically-insulating, both can be electrically-conductive, or one can be electrically-insulating and the other can be electrically-conductive. The electrical properties of the PCM members can be selected to achieve the desired degree of electrical insulation or electrical conductivity. For example, the PCM members can have a dielectric strength of at least about 100 V/mil, at least about 200 V/mil, at least about 500 V/mil, at least about 1000 V/mil, at least about 5000 V/mil, and/or at least about 10000 V/mil. The dielectric strength can be measured using the ASTM D149 test method.

While a bipolar RF energy end effector 110 is shown, it will be appreciated that the teachings herein can be readily applied in other types of electrosurgical devices, including those configured to provide monopolar RF energy, ultrasonic energy, or any combination thereof to a tissue section.

Various components of the devices disclosed herein can be constructed from any of a variety of known materials. Exemplary materials include those which are suitable for use in surgical applications, including metals such as stainless steel, polymers such as PEEK, ceramics, and so forth.

As the above-described devices are merely exemplary embodiments, it will be appreciated that the features of any particular device can be incorporated into any other device without departing from the scope of the present disclosure.

Various embodiments of electrosurgical devices that utilize therapeutic and/or sub-therapeutic electrical energy to treat tissue are disclosed herein. These embodiments can be configured for use in a manual or hand-operated manner, or can be utilized in robotic applications.

In operation, the end effector 110 can be positioned by a surgeon or other user at a surgical site. The end effector 110 can be positioned through, for example, endoscopic, laparoscopic, or open surgery techniques. The surgeon can position a tissue section between the first and second jaws 112, 114 and can operate an actuator, such as, for example, the trigger 118 coupled to the handle portion 106, to cause the jaws to rotate or otherwise transition to a closed position to grasp the tissue section between the first and second jaws. The tissue can thus be positioned between the jaws such that the electrodes 134, 140 are in contact with the tissue. The surgeon can subsequently activate delivery of energy to one or both of the electrodes. The delivered energy can include at least one of monopolar electrosurgical energy, bipolar electrosurgical energy, ultrasonic energy, thermal energy, and combinations thereof. The electrodes can deliver the energy to the tissue section grasped between the first and second jaws. The delivered energy can seal, weld, cauterize, dissect, and/or otherwise treat the tissue section. A cutting knife slidably receivable within a longitudinal channel 144 formed in the end effector can be deployable to cut the tissue section before, during, or after treatment of the tissue.

The temperature of the electrodes 134, 140 rises as energy is delivered thereto, causing the PCM members 136, 142 to change phase to a softened or molten state, wetting the interfaces between the electrodes and the body portions 132, 138 of the jaws. The PCM members can thus create a thin, low thermal resistance interface and improve the consistency and degree of heat transfer away from the electrodes. The PCM members 136, 142 can be configured such that, even in the molten state, they do not flow out from the interface between the electrodes 136, 142 and the body portions 132, 138 of the jaws. While not required, the end effector 110 can also include various features to help retain the PCM members 136, 142 when in the molten state, such as a raised ridge that extends around the periphery of each PCM member or a recess in which each PCM member is seated.

As shown in FIG. 5, an exemplary method of delivering energy to tissue can include positioning an end effector with respect to tissue (S500). In particular, the method can include positioning an electrosurgical device having a jaw member with an electrode that is spaced from the jaw member by a layer of phase change material such that the electrode is in contact with the tissue. The method can also include applying energy to the tissue and to the electrode (S502), thereby heating the electrode and transitioning the layer of phase change material to a liquid (S504) through which heat is conducted away from the electrode and into the jaw member (S506).

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used device is obtained and if necessary cleaned. The device can then be sterilized. In one sterilization technique, the device is placed in a closed and sealed container, such as a plastic or TYVEK bag. The container and device are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

It is preferred that the device is sterilized. This can be done by any number of ways known to those skilled in the art including beta or gamma radiation, ethylene oxide, steam, and a liquid bath (e.g., cold soak).

Although the invention has been described by reference to specific embodiments, it should be understood that numerous changes can be made within the spirit and scope of the inventive concepts described. Accordingly, it is intended that the invention not be limited to the described embodiments, but that it have the full scope defined by the language of the following claims.

The invention claimed is:

1. An electrosurgical device, comprising:
   a handle portion;
   an elongate shaft extending distally from the handle portion; and
   an end effector coupled to a distal end of the elongate shaft, the end effector comprising a first jaw member, a first electrode, and a first phase change material (PCM) member disposed between the first jaw member and at least a portion of the first electrode;
   wherein the first PCM member is configured to wet the first electrode and the first jaw member when in use without flowing from an interface between the first electrode and the first jaw member.

2. The electrosurgical device of claim 1, wherein the first PCM member has a first surface to which at least a portion of the first electrode is attached and a second, opposite surface to which at least a portion of the first jaw is attached.

3. The electrosurgical device of claim 1, wherein the end effector includes a second jaw member, a second electrode, and a second PCM member disposed between the second jaw member and at least a portion of the second electrode.

4. The electrosurgical device of claim 3, wherein the first and second jaw members define a longitudinal channel, the end effector comprising a cutting knife slidably receivable within the longitudinal channel, wherein the cutting knife is deployable along the longitudinal channel.

5. The electrosurgical device of claim 1, wherein the first PCM member comprises a planar sheet.

6. The electrosurgical device of claim 1, wherein the first PCM member is formed from a ceramic filled wax.

7. The electrosurgical device of claim 1, wherein the first PCM member has a phase change temperature of about 50 degrees C. to about 60 degrees C.

8. The electrosurgical device of claim 1, wherein the first PCM member has a thickness of about 0.003 inches to about 0.100 inches.

9. The electrosurgical device of claim 1, wherein the first PCM member has a thickness of about 0.005 inches to about 0.020 inches.

10. The electrosurgical device of claim 1, wherein the first PCM member has a thickness of about 0.010 inches to about 0.015 inches.

11. The electrosurgical device of claim 1, wherein the first PCM member comprises a thixotropic material.

12. The electrosurgical device of claim 1, wherein the first PCM member and the first electrode are laminated to the first jaw.

13. The electrosurgical device of claim 1, wherein the first PCM member is a solid at room temperature and a liquid at operating temperatures.

14. The electrosurgical device of claim 1, wherein the end effector is operable to deliver at least one of monopolar electrosurgical energy, bipolar electrosurgical energy, thermal energy, and combinations thereof.

15. The electrosurgical device of claim 1, wherein the first PCM member is thermally conductive with high dielectric strength, providing electrical isolation between the first jaw member and at least a portion of the first electrode.

16. An end effector, comprising:
a first jaw assembly comprising a first body portion and a first electrode, at least a portion of the first electrode being separated from the first body portion by a first layer of phase change material;
wherein the first layer of phase chant e material is configured to wet the first electrode and the first body portion when in use without flowing from an interface between the first electrode and the first body portion; and
a second jaw assembly comprising a second body portion and a second electrode;
wherein the first jaw assembly and the second jaw assembly are operatively coupled to one another such that tissue can be grasped between the first and second electrodes and such that energy can be delivered to the tissue through at least one of the first and second electrodes.

17. The device of claim 16, wherein at least a portion of the second electrode is separated from the second body portion by a second layer of phase change material.

18. The device of claim 16, wherein the first layer of phase change material is formed from a ceramic filled wax.

19. A method of delivering energy to tissue, comprising:
positioning an electrosurgical device having a jaw member with an electrode that is spaced from the jaw member by a layer of phase change material such that the electrode is in contact with the tissue; and
applying energy to the tissue and to the electrode, thereby heating the electrode and transitioning the layer of phase change material to a liquid through which heat is conducted away from the electrode and into the jaw member,
wherein the layer of phase change material wets the electrode and the jaw member when the energy is applied without flowing from an interface between the electrode and the jaw member.

* * * * *